United States Patent
Nuggehalli et al.

(10) Patent No.: US 11,861,523 B2
(45) Date of Patent: *Jan. 2, 2024

(54) APPROACH FOR CLOUD EMR COMMUNICATION VIA A CONTENT PARSING ENGINE AND A STORAGE SERVICE

(71) Applicant: RICOH COMPANY, LTD., Tokyo (JP)

(72) Inventors: Jayasimha Nuggehalli, Sunnyvale, CA (US); James Woo, Los Altos, CA (US)

(73) Assignee: Ricoh Company, Ltd., Tokyo (JP)

( * ) Notice: Subject to any disclaimer, the term of this patent is extended or adjusted under 35 U.S.C. 154(b) by 1071 days.

This patent is subject to a terminal disclaimer.

(21) Appl. No.: 16/587,418

(22) Filed: Sep. 30, 2019

(65) Prior Publication Data

US 2021/0097487 A1    Apr. 1, 2021

(51) Int. Cl.
*G06Q 10/10*    (2023.01)
*G16H 15/00*    (2018.01)
*G06F 40/205*    (2020.01)
*G06V 30/413*    (2022.01)
*G06V 30/416*    (2022.01)
*G06V 30/40*    (2022.01)
(Continued)

(52) U.S. Cl.
CPC ........... *G06Q 10/10* (2013.01); *G06F 40/205* (2020.01); *G06V 30/1456* (2022.01); *G06V 30/40* (2022.01); *G06V 30/413* (2022.01); *G06V 30/416* (2022.01); *G16H 15/00* (2018.01); *G06V 30/10* (2022.01)

(58) Field of Classification Search
CPC ...... G06Q 10/10; G16H 15/00; G06F 40/205; G06V 10/25; G06V 30/413; G06V 30/416
See application file for complete search history.

(56) References Cited

U.S. PATENT DOCUMENTS

| | | |
|---|---|---|
| 5,390,259 A | 2/1995 | Withgott |
| 5,832,100 A | 11/1998 | Lawton |
| 7,840,891 B1 | 11/2010 | Yu |

(Continued)

OTHER PUBLICATIONS

Nuggehalli, U.S. Appl. No. 16/355,630, filed Mar. 15, 2019, Final Office Action dated Apr. 15, 2020.
(Continued)

*Primary Examiner* — Aryan E Weisenfeld
(74) *Attorney, Agent, or Firm* — Hickman Becker Bingham Ledesma LLP

(57) ABSTRACT

An approach provides sending captured Superbill image data and output data generated based on results of parsing the captured Superbill image data to an external system which manages Superbill data via a cloud system and a storage service. The cloud system creates parsing rule data for parsing a captured Superbill image in accordance with user operation at a client device. The cloud system obtains captured Superbill image data from the storage service, in response to receiving a notification indicating that the captured Superbill image data has been stored in the storage service. The cloud system parses the obtained image data based on the created parsing rule and generates output data based on results of parsing. The cloud system sends the generated output data and the obtained image data to the external system via the one or more computer networks.

20 Claims, 15 Drawing Sheets

(51) Int. Cl.
*G06V 30/14* (2022.01)
*G06V 30/10* (2022.01)

(56) References Cited

U.S. PATENT DOCUMENTS

| | | | |
|---|---|---|---|
| 9,984,471 | B2 | 5/2018 | Becker |
| 10,114,906 | B1 | 10/2018 | Becker |
| 10,354,134 | B1 | 7/2019 | Becker |
| 2001/0016068 | A1* | 8/2001 | Shibata ............... G06V 10/22 382/195 |
| 2005/0062991 | A1 | 3/2005 | Fujishige |
| 2007/0294614 | A1 | 12/2007 | Jacquin |
| 2008/0115057 | A1 | 5/2008 | Grandhi |
| 2011/0078098 | A1 | 3/2011 | Lapir |
| 2011/0249286 | A1 | 10/2011 | Sue |
| 2011/0270760 | A1* | 11/2011 | Graham, III ......... G06Q 40/00 705/51 |
| 2012/0303636 | A1 | 11/2012 | Luo |
| 2013/0036347 | A1 | 2/2013 | Eftekhari |
| 2013/0194613 | A1 | 8/2013 | Link |
| 2014/0229312 | A1 | 8/2014 | Nuggehalli |
| 2014/0241631 | A1 | 8/2014 | Huang |
| 2014/0268250 | A1 | 9/2014 | Nepomniachtchi |
| 2015/0146984 | A1 | 5/2015 | Brown |
| 2015/0256712 | A1 | 9/2015 | Wshah |
| 2016/0216851 | A1 | 7/2016 | Kanivets |
| 2016/0274745 | A1 | 9/2016 | Baba |
| 2016/0283444 | A1 | 9/2016 | Briggs |
| 2017/0070623 | A1 | 3/2017 | Uchida |
| 2017/0372439 | A1 | 12/2017 | Smith |
| 2018/0025222 | A1 | 1/2018 | Yellapragada |
| 2018/0107755 | A1 | 4/2018 | Zholudev |
| 2018/0330202 | A1 | 11/2018 | Blanchflower |
| 2019/0050639 | A1* | 2/2019 | Ast ..................... G06V 10/82 |
| 2019/0095709 | A1 | 3/2019 | Hara |
| 2019/0251192 | A1 | 8/2019 | Govindaraj |
| 2020/0296246 | A1* | 9/2020 | Nuggehalli .......... G06V 30/412 |

OTHER PUBLICATIONS

Nuggehalli, U.S. Appl. No. 15/355,629, filed Mar. 15, 2019, Notice of Allowance dated Mar. 4, 2020.

Nuggehalli, U.S. Appl. No. 16/355,630, filed Mar. 15, 2019, Office Action dated Dec. 16, 2019.

Nuggehalli, U.S. Appl. No. 16/355,629, filed Mar. 15, 2019, Office Action dated Nov. 21, 2019.

* cited by examiner

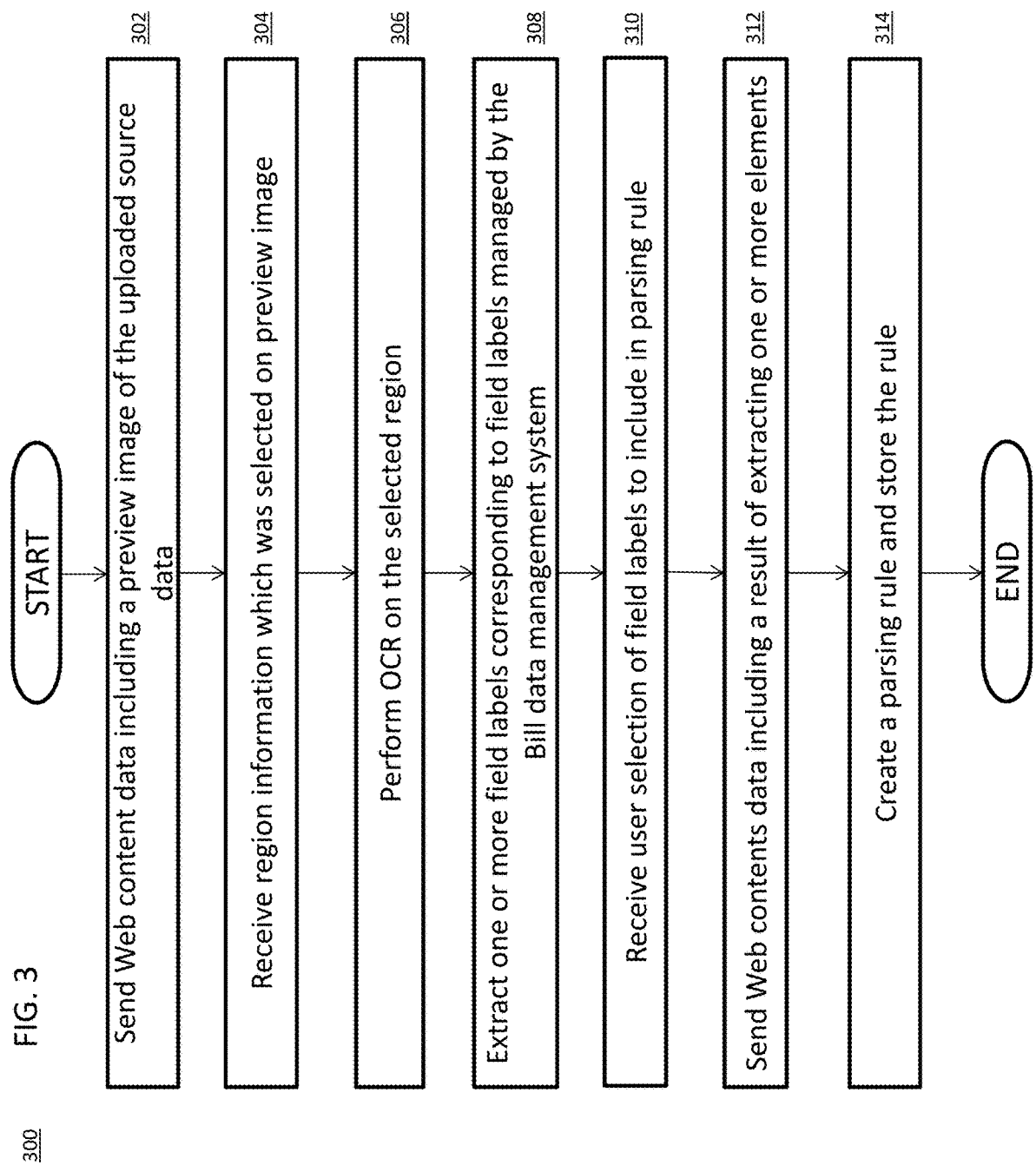

Login View

Parsing rule view

Parsing area selection view

Element detection view

Bibliographic information setting view

Parsing rule creating view

APPROACH FOR CLOUD EMR COMMUNICATION VIA A CONTENT PARSING ENGINE AND A STORAGE SERVICE

RELATED APPLICATION DATA AND CLAIM OF PRIORITY

This application is related to U.S. patent application Ser. No. 16/355,629 entitled "APPROACH FOR CLOUD EMR COMMUNICATION VIA A CONTENT PARSING ENGINE", filed Mar. 15, 2019, and U.S. patent application Ser. No. 16/355,630 entitled "APPROACH FOR CLOUD EMR COMMUNICATION VIA A CONTENT PARSING ENGINE AND A STORAGE SERVICE", filed Mar. 15, 2019, the contents all of which are incorporated by reference in their entirety for all purposes as if fully set forth herein.

FIELD

Embodiments relate generally to processing electronic documents. SUGGESTED GROUP ART UNIT: 2625; SUGGESTED CLASSIFICATION: 358.

BACKGROUND

The approaches described in this section are approaches that could be pursued, but not necessarily approaches that have been previously conceived or pursued. Therefore, unless otherwise indicated, the approaches described in this section may not be prior art to the claims in this application and are not admitted prior art by inclusion in this section.

The continued growth of network services, and in particular Internet-based services, provides access to an ever-increasing amount of functionality. Cloud services in particular continue to grow into new areas. One of the issues with cloud services is that they can be difficult to use with certain types of end-user devices, such as multi-function peripherals (MFPs) for several reasons. First, assuming that end-user devices have the requisite computing capability, some cloud services have interfaces that require a high level of programming skill and customization to implement on end-user devices. In addition, implementing a workflow that uses multiple cloud services requires an even higher level of skill and knowledge because each service has different settings requirements and the results of one cloud service have to be stored, reformatted, and provided to another cloud service. Further, some cloud services require that certain data, such as user authorization data, be maintained on the client side, e.g., at an MFP, which is unpractical and, in some situations, not possible.

SUMMARY

An apparatus comprises one or more processors, and one or more memories communicatively coupled to the one or more processors. The one or more processors receive source data of a sample Superbill via one or more computer networks from a client device. The one or more processors create parsing rule data for parsing a Superbill which is based on the received source data by a user operation on the client device. The parsing rule data include at least region information where data in one or more data fields should be extracted from the Superbill and one or more field labels to be associated with the extracted data in the one or more data fields. The one or more field labels are managed by a first external system which manages Superbill data. The one or more processors access, via the one or more computer networks, a second external system which stores data, to detect whether actual captured Superbill image data has been stored in the second external system. The one or more processors obtain the image data via the one or more computer networks from the second external system. The one or more processors parse the obtained image data based on the created parsing rule data. The one or more processors generate output data based on a parsing result of which the obtained image data is parsed. The one or more processors send, via the one or more computer networks to the external system, the generated output data and the obtained image data.

Embodiments may be implemented by one or more non-transitory computer-readable media and/or one or more computer-implemented methods.

BRIEF DESCRIPTION OF THE DRAWINGS

In the figures of the accompanying drawings like reference numerals refer to similar elements. Embodiments of the disclosure have other advantages and features which will be more readily apparent from the following detailed description and the appended claims, when taken in conjunction with the examples in the accompanying drawings, in which:

FIG. 3 is a flow diagram that depicts a process for creating a parsing rule.

DETAILED DESCRIPTION

In the following description, for the purposes of explanation, numerous specific details are set forth in order to provide a thorough understanding of the embodiments. It will be apparent, however, to one skilled in the art that the embodiments may be practiced without these specific details. In other instances, well-known structures and devices are shown in block diagram form to avoid unnecessarily obscuring the embodiments.

Figure 1:
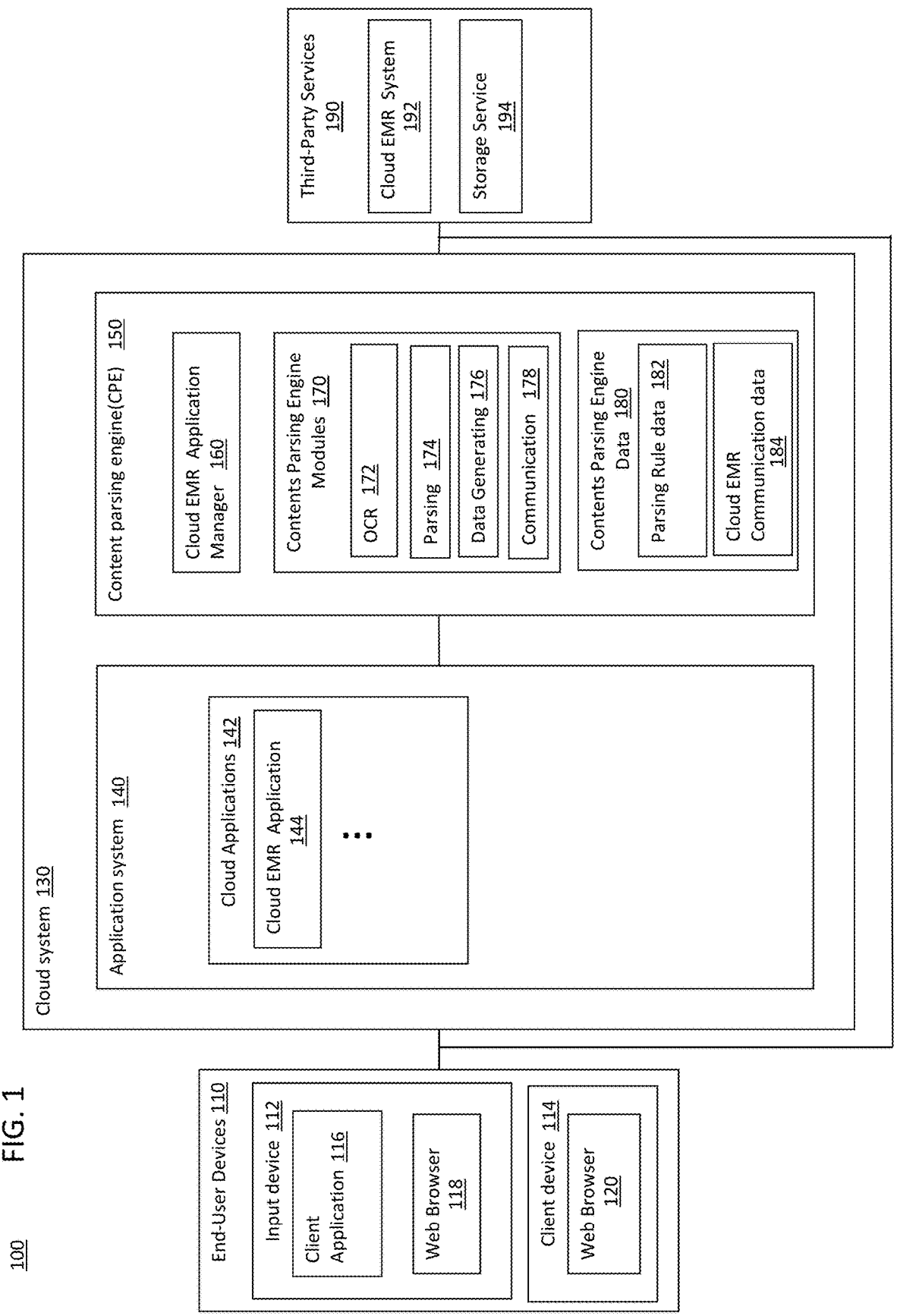
FIG. 1 is a block diagram that depicts an arrangement for accessing cloud services using end-user devices.

FIG. 1 is a block diagram that depicts an arrangement 100 for accessing cloud services using end-user devices. In the example depicted in FIG. 1, arrangement 100 includes end-user devices 110, a Cloud System 130, and third-party services 190. This approach is depicted in the context of preparing Superbill data for sending, through Application System 140 and Storage Service 194, to Cloud Electronic Medical Record (EMR) system 192 which is included in third-party services 190 and manages Superbill data. As used herein, the term "Superbill" refers to an itemized form used by healthcare providers that details services provided to a patient. Superbills typically include information about the provider, the patient, and the type of care provided, and are commonly used to create healthcare claims that are submitted to payers for reimbursement.

End-user devices 110 include one or more input devices 112 and one or more client devices 114. According to one embodiment, an input device 112 is a device that performs capturing of a Superbill image, such as scanner device, a smart device, etc. According to another embodiment, a client device 114 is a device that may perform displaying of an operation screen for creating, deleting or editing a parsing rule for parsing a Superbill image which is captured, such as on a web browser. End-user devices 110 may include computer hardware, computer software, and any combination of computer hardware and computer software for performing capturing an image. This may include, for example, scanning components, one or more processors, one or more memories, one or more communications interfaces, such as wired and wireless interfaces, an operating system, one or more processes for supporting and performing the functionality provided by end-user devices 110, a display such as a touch screen display, etc. According to one embodiment, end-user devices 110 include one or more elements for communicating with other processes. In the example depicted in FIG. 1, a client device 114 may include a Web browser 120. An input device 110 may include a client application 116, or alternatively, a Web browser 118. The client application 116 is an application that is configured to communicate with Cloud System 130 and implements at least a portion of one or more application program interfaces (APIs) of Cloud System 130. For example, a client application 116 may implement Web browser functionality to communicate with Cloud System 130. Web browser 118 and Web browser 120 may be any type of Web browser for communicating with Cloud System 130 and allows end-user devices 110 to access functionality provided by Cloud System 130.

Cloud System 130 is a cloud environment that includes an Application System 140 and a Content Parsing Engine (CPE) 150. Cloud System 130 may be implemented on one or more computing elements, such as network elements, servers, etc., and embodiments are not limited to any particular implementation for Cloud System 130. Cloud System 130 may include fewer or additional elements than the elements depicted in FIG. 1, depending upon a particular implementation, and Cloud System 130 is not limited to any particular implementation. For example, Cloud System 130 may be implemented by one or more processes executing on one or more computing systems.

Cloud System 130 includes cloud applications 142. Cloud applications 142 may be managed by one or more application server processes. Cloud applications 142 may include a wide variety of applications for performing various functions, including as connectors to services provided by Content Parsing Engine (CPE) 150, as described in more detail hereinafter. In the example depicted in FIG. 1, Cloud applications 142 include at least a Cloud EMR application 144. Cloud EMR application 144 provides a user interface to a user of end-user devices 110 and access to Cloud EMR application 144 in Cloud system 130. Third-party services 190 included Cloud EMR system 192 and Storage Service 194. Cloud EMR system 192 may have specific requirements for registering Superbill data on Cloud EMR system 192 including, for example, formatting requirements, bibliographical information, etc. Bibliographical information to be registered on Cloud EMR system 192 has to be in accordance with items managed by Cloud EMR system 192. Storage Service 194 provides a storage service to store data. Storage Service 194 may have a storage device to store data and a notification function which sends, to external services, such as Cloud EMR application 144, a notification indicating data has been stored in the storage device.

Embodiments are not limited to this application and other applications may be provided, depending upon a particular implementation. One example application not depicted in FIG. 1 is an application for converting data for mobile applications, e.g., a PDF conversion application for mobile printing.

CPE 150 includes a Cloud EMR Application Manager 160, Content Parsing Engine (CPE) modules 170 and Content Parsing Engine (CPE) data 180. CPE may be implemented on one or more computing elements, such as network elements, servers, etc., and embodiments are not limited to any particular implementation for CPE 150. CPE 150 may include fewer or additional elements than the elements depicted in FIG. 1, depending upon a particular implementation, and CPE 150 is not limited to any particular implementation. For example, CPE 150 may be implemented by one or more processes executing on one or more computing systems.

Cloud EMR Application Manager 160 manages processes including at least processing of parsing controlling, processing of requests to and from Application System 140 and third-party services 190, and performing various administrative tasks for CPE 150. Further, Cloud EMR Application Manager 160 manages creating, editing and deleting Parsing rule data 182.

CPE modules 170 are processes that each implement one or more functions. The functions may be any type of function and may vary depending upon a particular implementation. According to one embodiment, the functions include input functions, output functions, and process functions. In the example depicted in FIG. 1, CPE modules 170 include several functions, including OCR 172, Parsing 174, Data Generating 176 and Communication 178. OCR 172 provides OCR. Parsing 174 provides parsing of image data. Data Generating 176 provides to generate output data for sending to third-party services 190. Communication 178 provides CPE 150 communication with third-party services 190. These example modules are provided for explanation purposes and embodiments are not limited to these example modules. CPE modules 170 may be used by other processes to perform the specified function. For example, an application external to Cloud system 130 may use OCR 172 to convert image data to text using optical character recognition, although this requires that the application implement the API of OCR 172.

Content Parsing Engine (CPE) data 180 includes data used to configure and manage CPE 150. In the example depicted in FIG. 1, CPE data 180 includes Parsing Rule data 182 and Cloud EMR Communication data 184. Parsing Rule data 182, for example, may include a rule for parsing image data including at least information relating to an area of a Superbill from which information may be extracted so that OCR may be performed on the extracted information. Cloud EMR Communication data 184 may include information indicating where data may be sent to Cloud EMR system 192 included in third-party services 190. This data may include, for example, Uniform Resource Identifier (URI) of Web-API or FTP address. This data is used, for example, to access Cloud EMR system 192, as described in more detail hereinafter.

Figure 2:
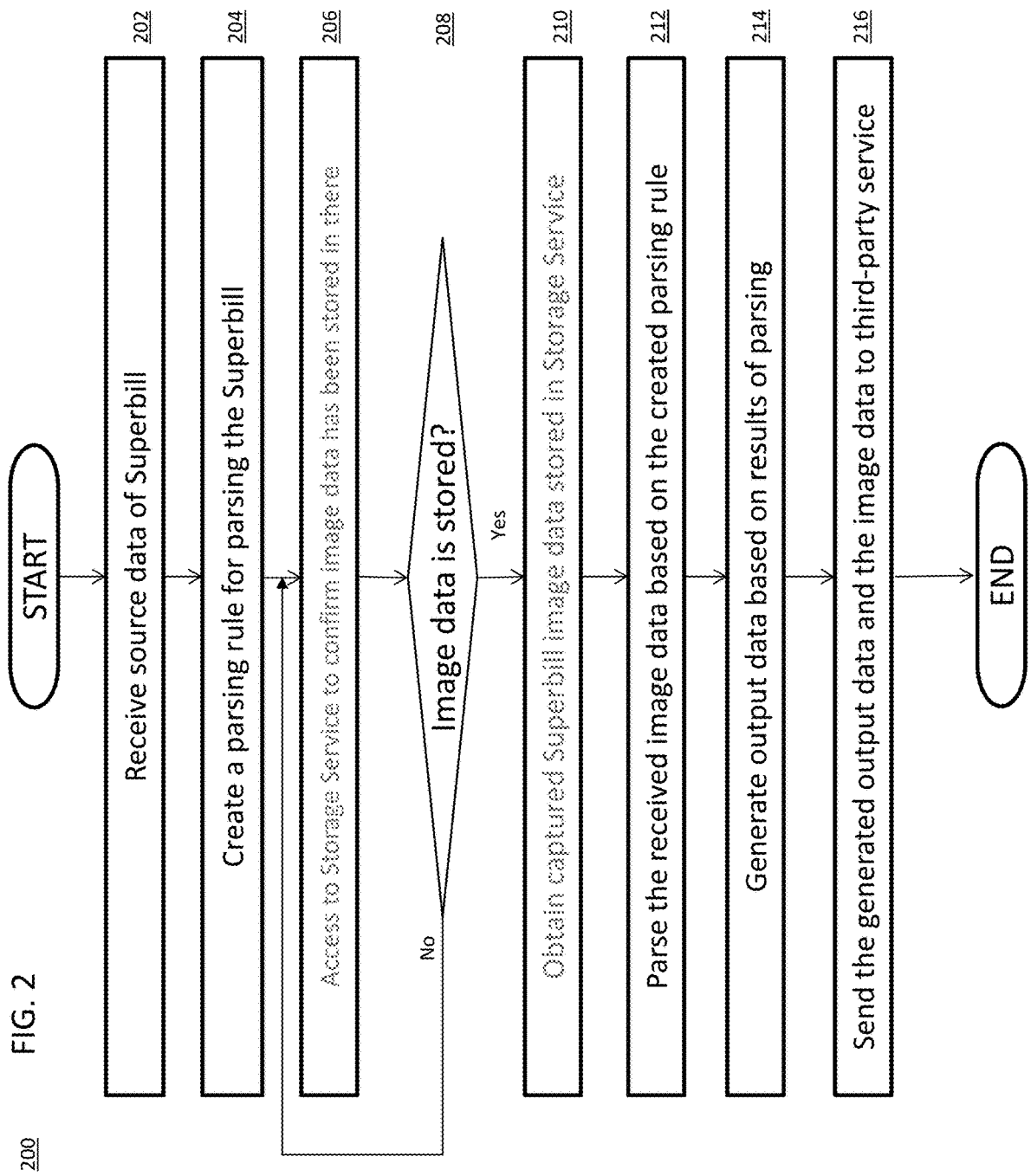
FIG. 2 is a flow diagram that depicts an approach for uploading and registering Superbill data to a cloud service.

FIG. 2 is a flow diagram 200 that depicts an approach for uploading and registering Superbill data captured by Input device 112 to Cloud EMR system 192. In step 202, Cloud EMR Application Manager 160 receives Superbill source data from Client device 114. For example, Cloud EMR Application Manager 160 provides a user interface to Web Browser 120 of Client device 114 via a network. The user interface receives an input of Superbill source data. This Superbill source data is sample data that will be used to create a parsing rule in step 204. A communication protocol between Cloud EMR Application Manager 160 and Web Browser 120 is, for example, Hyper Text Transfer Protocol (HTTP) or Hypertext Transfer Protocol Secure (HTTPS). In step 204, Cloud EMR Application Manager 160 creates a parsing rule for parsing a Superbill image based on the Superbill source data which has been received from Client device 114. The created parsing rule may be stored as Parsing Rule Data 182 in CPE Data 180. The creation process of the parsing rule for parsing a Superbill image is described in more detail hereinafter.

After creating the parsing rule, in step 206, Cloud EMR application 144 accesses to Storage Service 194 to detect whether Superbill image data has been stored. Accessing to Storage Service 194 may be through Web API provided by Storage Service 194. Cloud EMR application 144 repeats accessing to Storage Service 194 during the time that the Cloud EMR application 144 does not detect that Superbill image data has been stored. Timing of repeat accessing may be performed by polling at predetermined timing. The predetermined timing may be a certain interval for example every one second. The stored image data is actual Superbill image data, as opposed to the sample Superbill image data obtained in step 202 to create the parsing rule in step 204. The image data stored in Storage Service 194 is received from an Input device 112. The image data sent from Input device 112 is Superbill image data captured by Input device 112 or another capturing device.

In response to detecting that Superbill image has been stored in step 208, Cloud EMR application 144 obtains the image data stored in Storage Service 194 from Storage Service 194 in step 210. Cloud EMR application 144, for example, accesses Storage Service 194 via a Web API provided by Storage Service 194 and downloads the image data from Storage Service 194. Cloud EMR application 144 transfers the obtained image data to CPE 150 through a network. For example, the image data may be transferred via Web Application Programing Interface (API) provided by CPE 150. In step 212, CPE 150 parses the image data transferred from Cloud EMR application 144 based on Parsing Rule data 182. In detail, OCR module 172 performs OCR on a region of the image data defined by Parsing Rule data 182. After OCR is performed, Parsing module 174 conducts a parsing process on the result of the OCR process in accordance with Parsing Rule data 182.

In step 214, CPE 150 generates output data for sending to Cloud EMR System 192 based on results of the parsing process. In detail, Data Generating module 176 generates output data suitable for a communication user interface provided by Cloud EMR System 192. Output data, for example, may be generated by Extensible Markup Language (XML). The communication interface may include, for example, Web API of Cloud EMR System 192. In step 216, CPE 150 sends, to Cloud EMR System 192 through a network, the generated output data and the image data transferred from Cloud EMR application 144. The output data and the image data may be sent via Web API of Cloud EMR System 192. Alternatively, the output data and the image data may be sent via different interfaces. For example, the output data may be sent via Web API of Cloud EMR System 192 and the image data may be sent using a file transfer protocol (FTP).

Figure 4A:
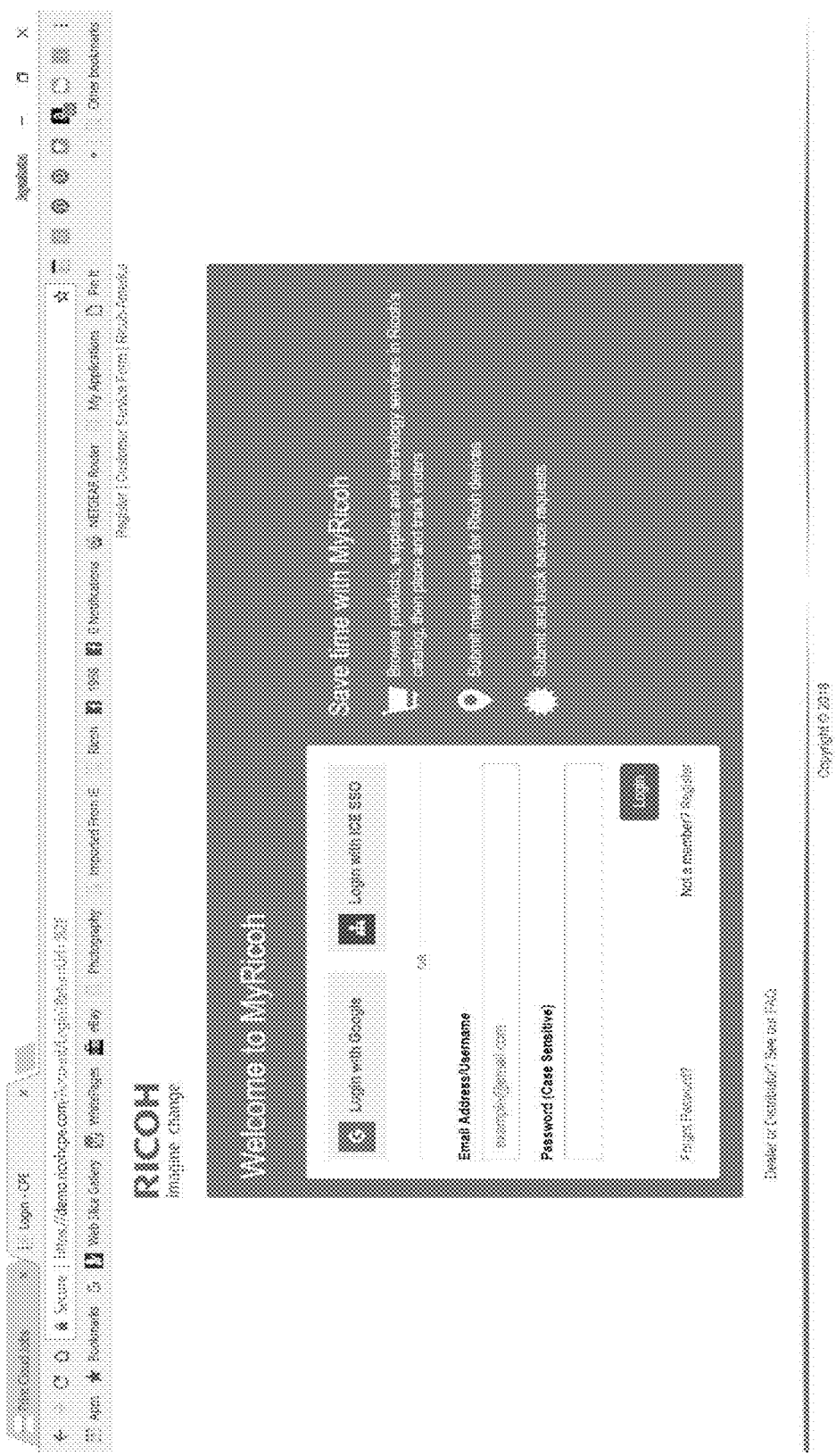
FIG. 4A is a user interface screen that allows a user to login to a Cloud EMR (Electronic Medical Records) application Manager.
Figure 4B:
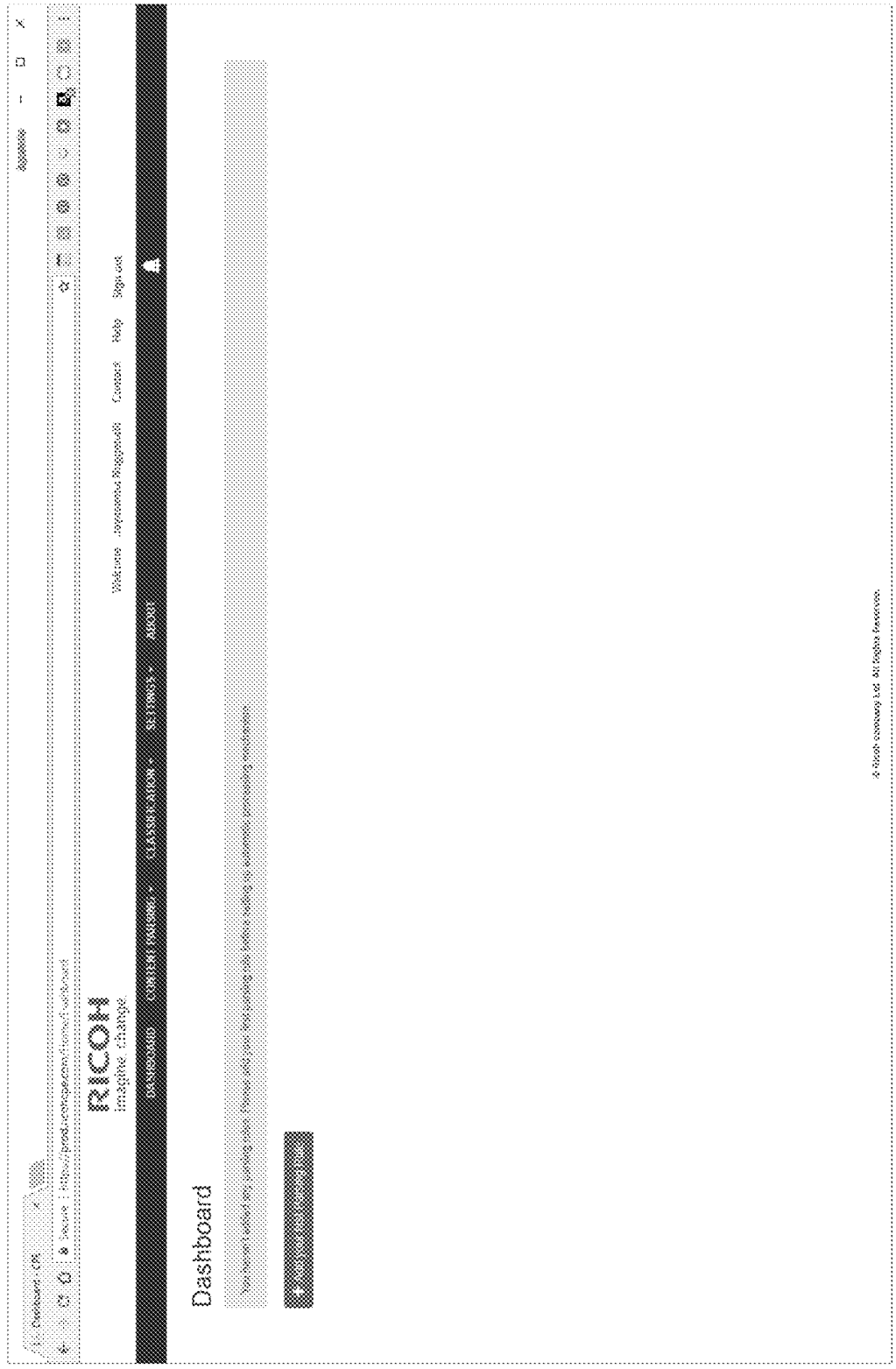
FIG. 4B is a user interface screen that displays a parsing rule list for parsing Superbill data.
Figure 4C:
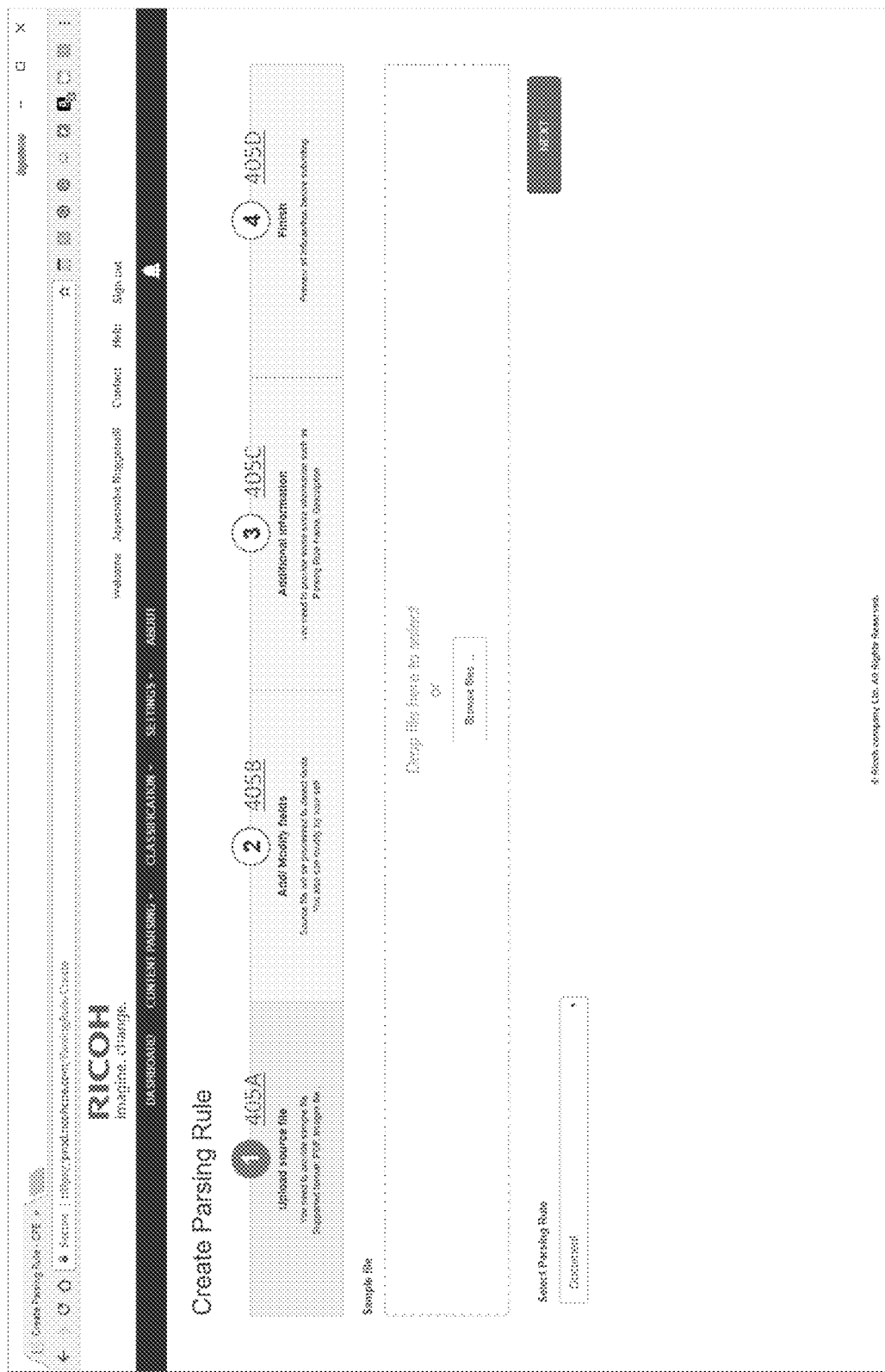
FIG. 4C is a user interface screen that allows a user to create a parsing rule.
Figure 4D:
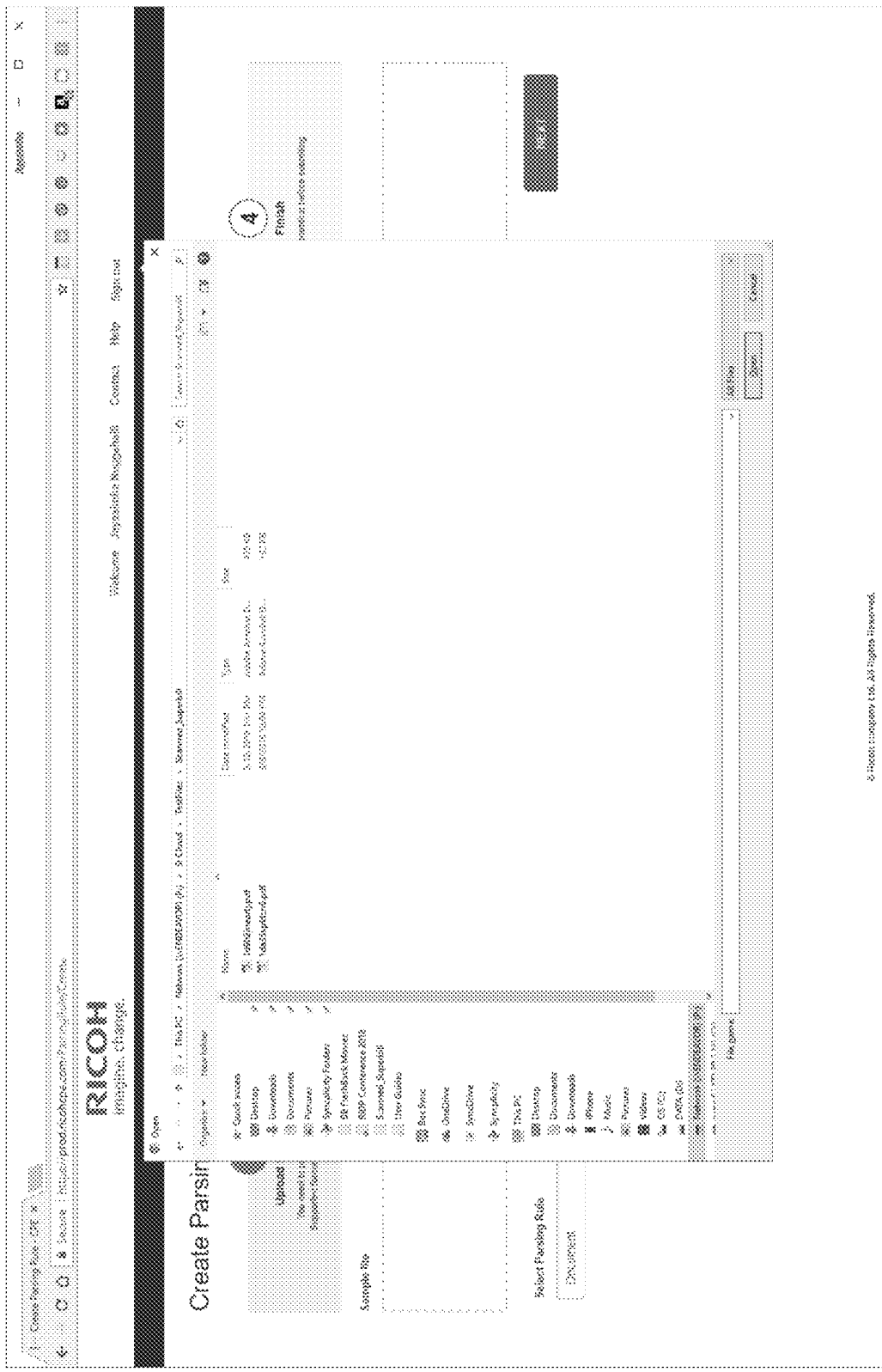
FIG. 4D is a user interface screen that allows a user to select Superbill data to be uploaded on a Cloud EMR application Manager.
Figure 4E:
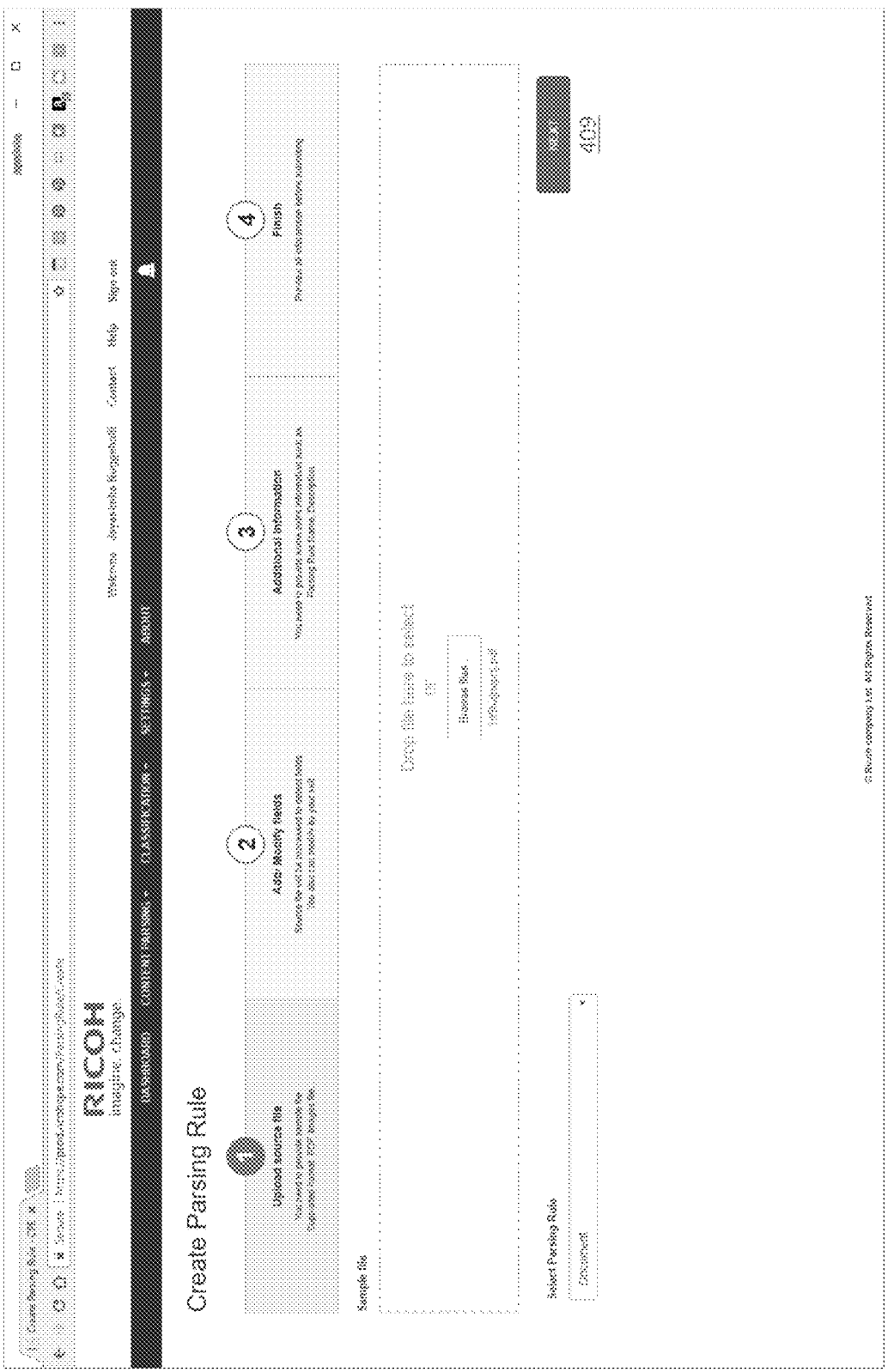
FIG. 4E is a user interface screen that displays identification information of the selected Superbill data to be uploaded.
Figure 4F:
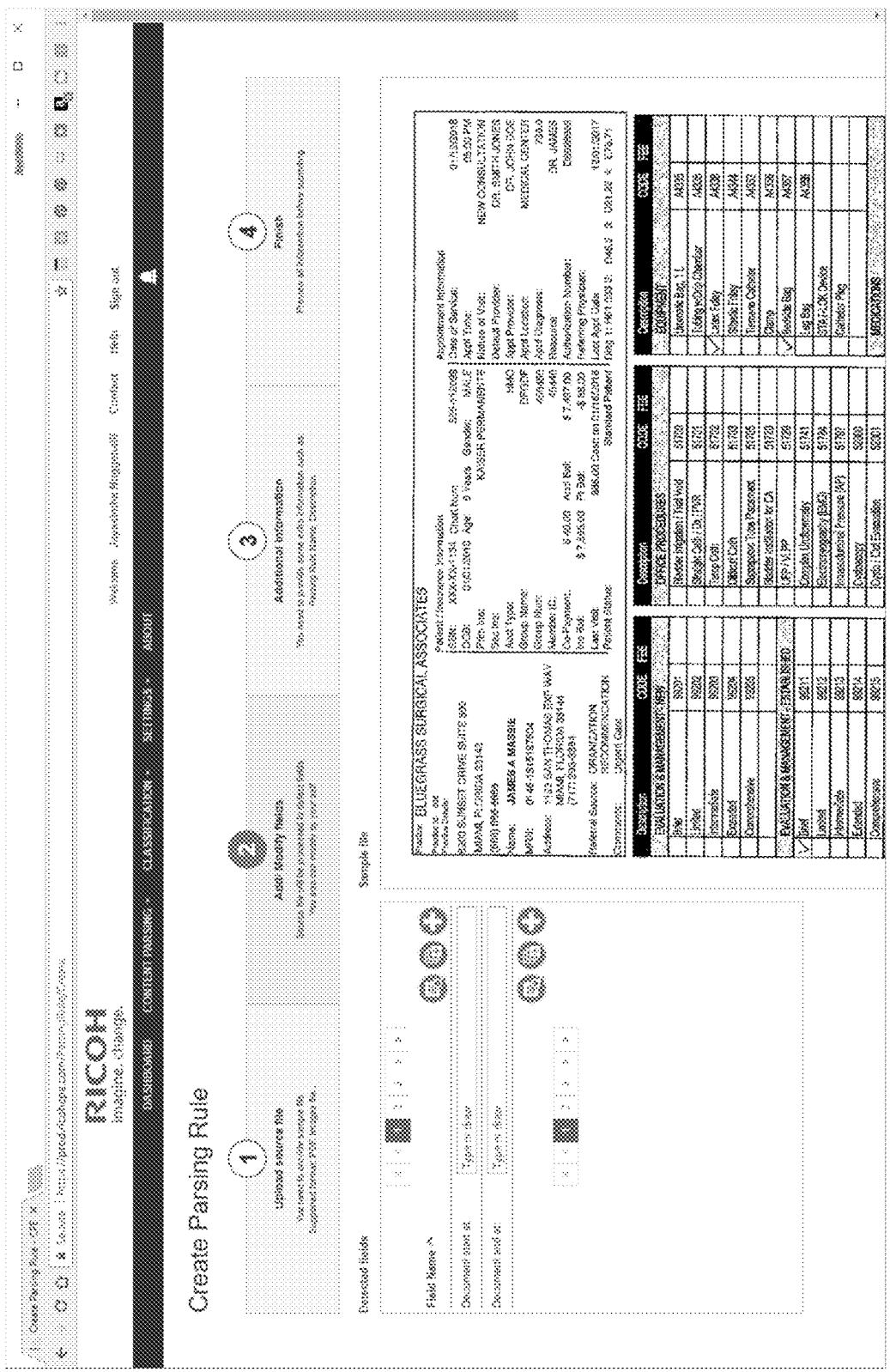
FIG. 4F is a user interface screen that displays a preview image of Superbill source data.

FIG. 3 is a flow diagram 300 that depicts a process for creating parsing rule for parsing a Superbill image by user operation on Web browser 120. The detail of the creation process is described with reference to the user interface shown in FIG. 4. In step 302, Cloud EMR Application Manager 160 sends Web content data including a preview image of Superbill source data to Web browser 120 in response to receiving the source data from Web browser as described in step 202. FIG. 4A through FIG. 4F are user interface screens which receive an input of Superbill source data and display a preview image of the source data on Web Browser 120. FIG. 4A is a user interface screen 400 that allows a user to login to Cloud EMR Application Manager 160 for receiving an input of User ID and Password from a user of Client device 114. FIG. 4B is a user interface screen 402 that displays a parsing rule list for parsing Superbill data. For example, the user interface screen 402 is shown in response to a successful login of the user on the user interface screen 402. In this example, the user has not yet added any parsing rules, so no parsing rules are listed on the screen. The user of Client device 114 starts to create a parsing rule on the user interface screen 402. FIG. 4C is a user interface screen 404 that allows a user to create a parsing rule. For example, a four-step process is shown. The first step 405A is for the user to upload a source file, such as a PDF or other document upon which OCR can be performed. The second step 405B is for the user to add or modify one or more field labels in the parsing rule. The source file will be processed to detect the one or more field labels, but the user can also add or modify the one or more field labels. The third step 405C is for the user to add additional information, such as parsing rule name or description. The fourth step 405D is for the user to finish, which means preview the parsing rule before submitting it. FIG. 4D is a user interface screen 406 that allows a user to select Superbill data to be uploaded on Cloud EMR Application Manager 160. This is the first step 405A shown in FIG. 4C. For example, the user selects a PDF file of Superbill data. The Superbill data may serve as the basis for creating one or more parsing rules. FIG. 4E is a user interface screen 408 that displays identification information of the selected Superbill data to be uploaded. After receiving user input on the user interface screen 408 to select the identified Superbill data, for example selection of the NEXT button 409, the selected Superbill data is sent to Cloud EMR Application Manager 160. FIG. 4F is a user interface screen 410 that displays a preview image of Superbill source data.

Figure 4G:
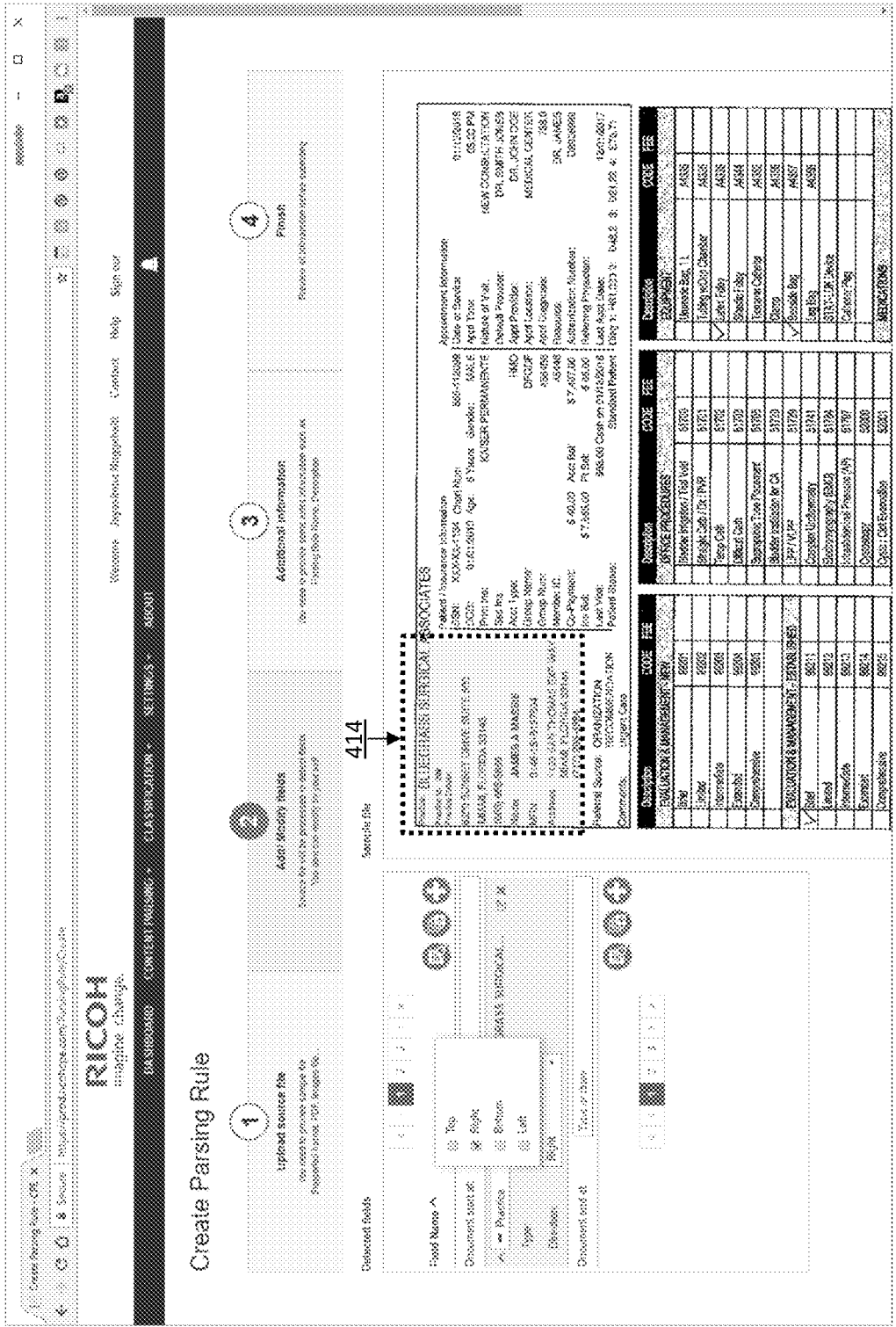
FIG. 4G is a user interface screen that allows a user to select a region of the Superbill.
Figure 4H:
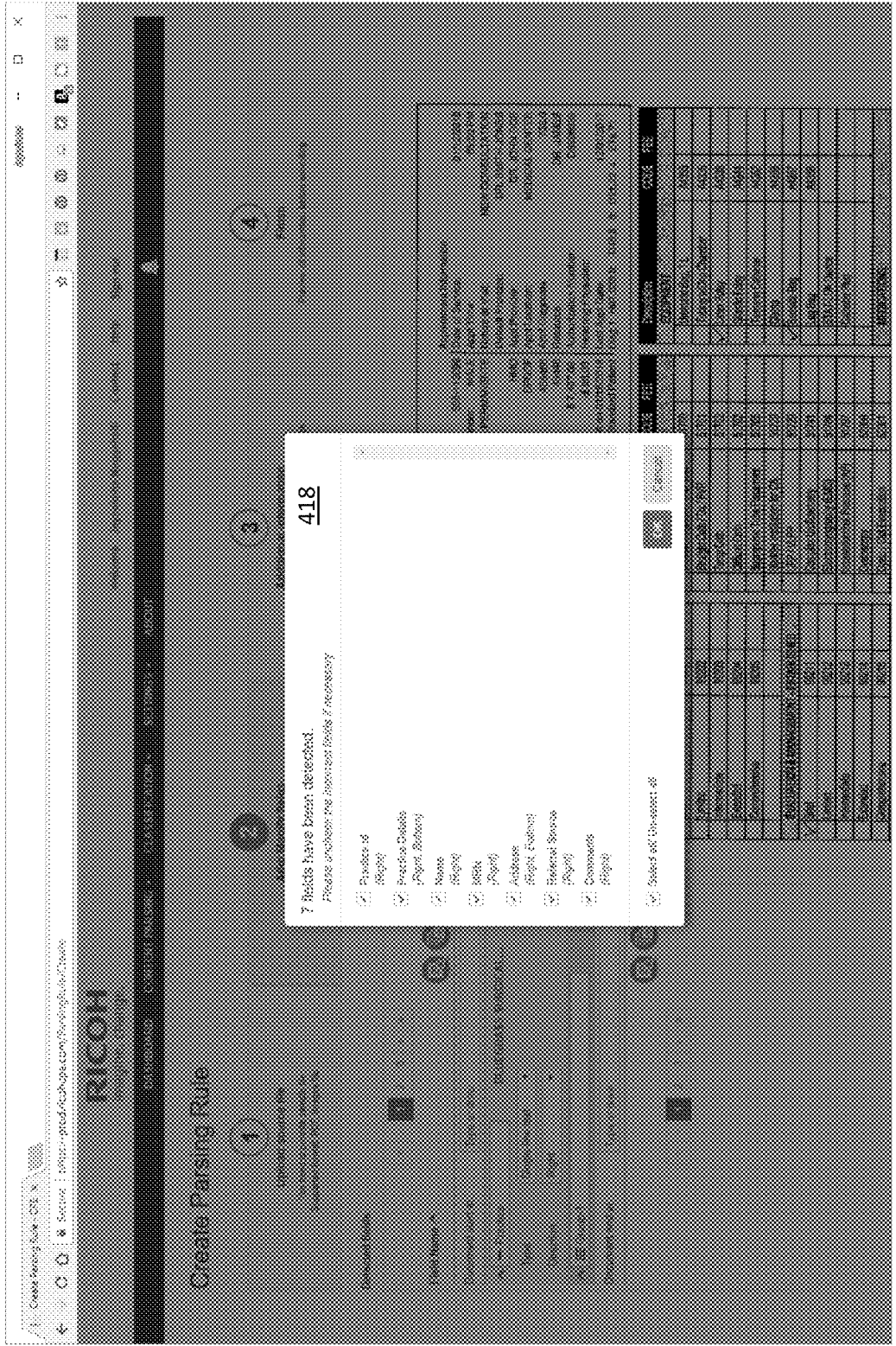
FIG. 4H is a user interface screen that allows a user to select or deselect the extracted one or more field labels.

In step 304, Cloud EMR Application Manager 160 receives region information which was selected on the displayed preview image on Web browser 120 by the user, for example, by using a computer mouse. FIG. 4G is a user interface screen 412 that allows a user to select a region of the Superbill. For example, a region 414 on the user interface screen 412 is a region which is selected by the user, for example by clicking on the region with a computer mouse. In this example, the user may also select where one or more data fields are located relative to the one or more field labels, such as "Name," "Address," etc. within region 414. In this example is a pop-up window showing options top, right, bottom or left for selection by the user. The user selected "right" in this example, meaning that the data fields are located to the right of field labels in region 414. In step 306, Cloud EMR Application Manager 160 performs OCR on the selected region 414. In step 308, Cloud EMR Application Manager 160 extracts the one or more field labels corresponding to field labels managed by a Bill data management system, for example, Cloud EMR System 192. The field labels may be prestored in CPE data 180, or alternatively obtained from Cloud EMR System 192 by accessing via a Web API of Cloud EMR System 192. FIG. 4H is a user interface screen 416 that allows a user to select or deselect the extracted one or more field labels. This is the second step 405B shown in FIG. 4C, where the user can add or modify data fields in the parsing rule. For example, the extracted one or more field labels may be displayed on a popup screen 418 on the user interface screen 416. In this example, extracted field labels from region 414 are listed, such as "Practice ID," "Practice Details," "Name," "MRN," "Address," "Referral Source," and "Comments." In step 310, Cloud EMR Application Manager 160 receives user selection of field labels to include in parsing rule via the popup screen 418. In this example, the user may then "Select All," "Unselect All," or select any number of the field labels to be added to the parsing rule.

Figure 4I:
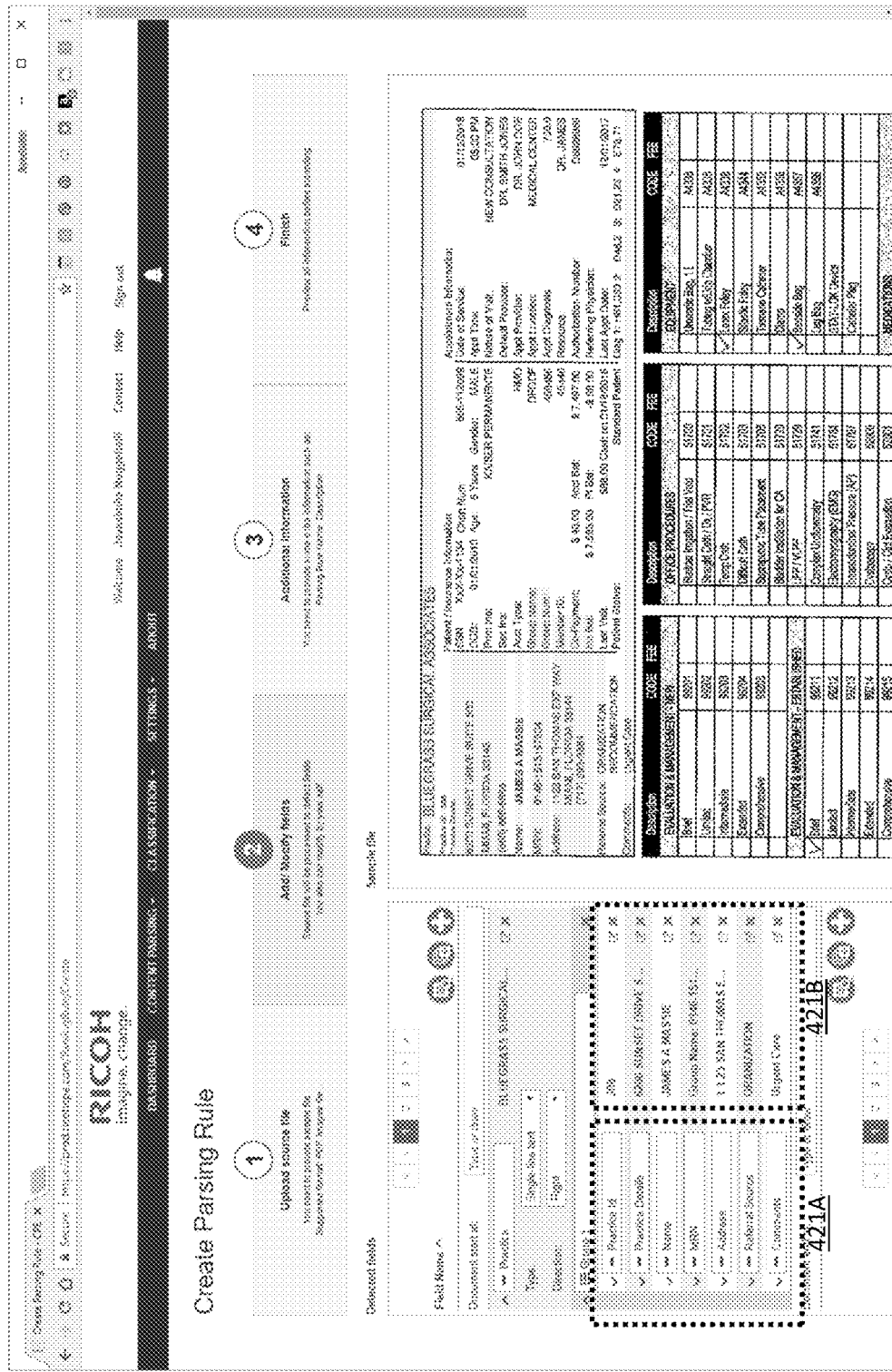
FIG. 4I is a user interface screen that displays the data in the data fields of the Superbill image that corresponds to the extracted one or more field labels selected by the user.
Figure 4J:
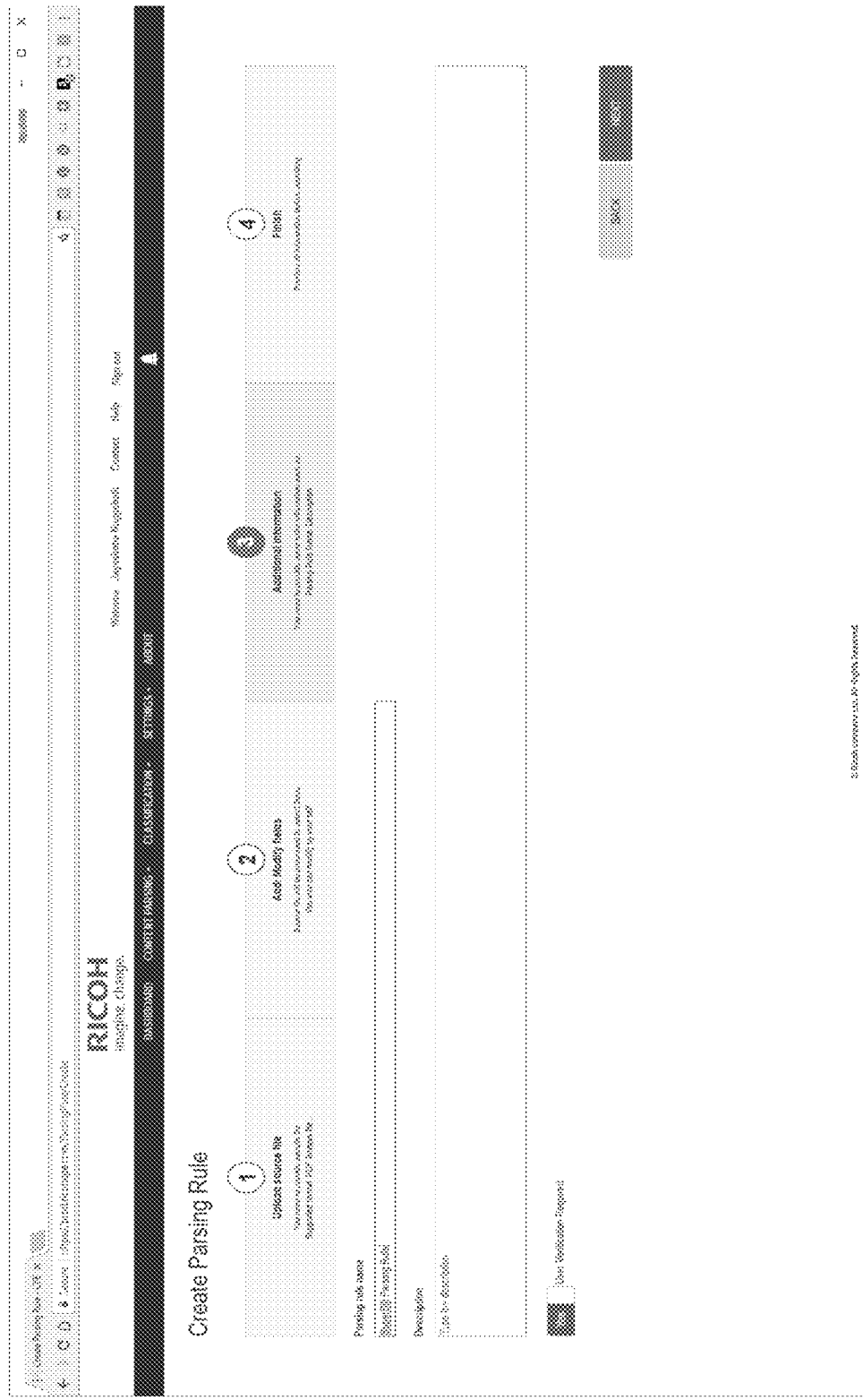
FIG. 4J is a user interface screen that allows a user to enter bibliographic information for the parsing rule.
Figure 4K:
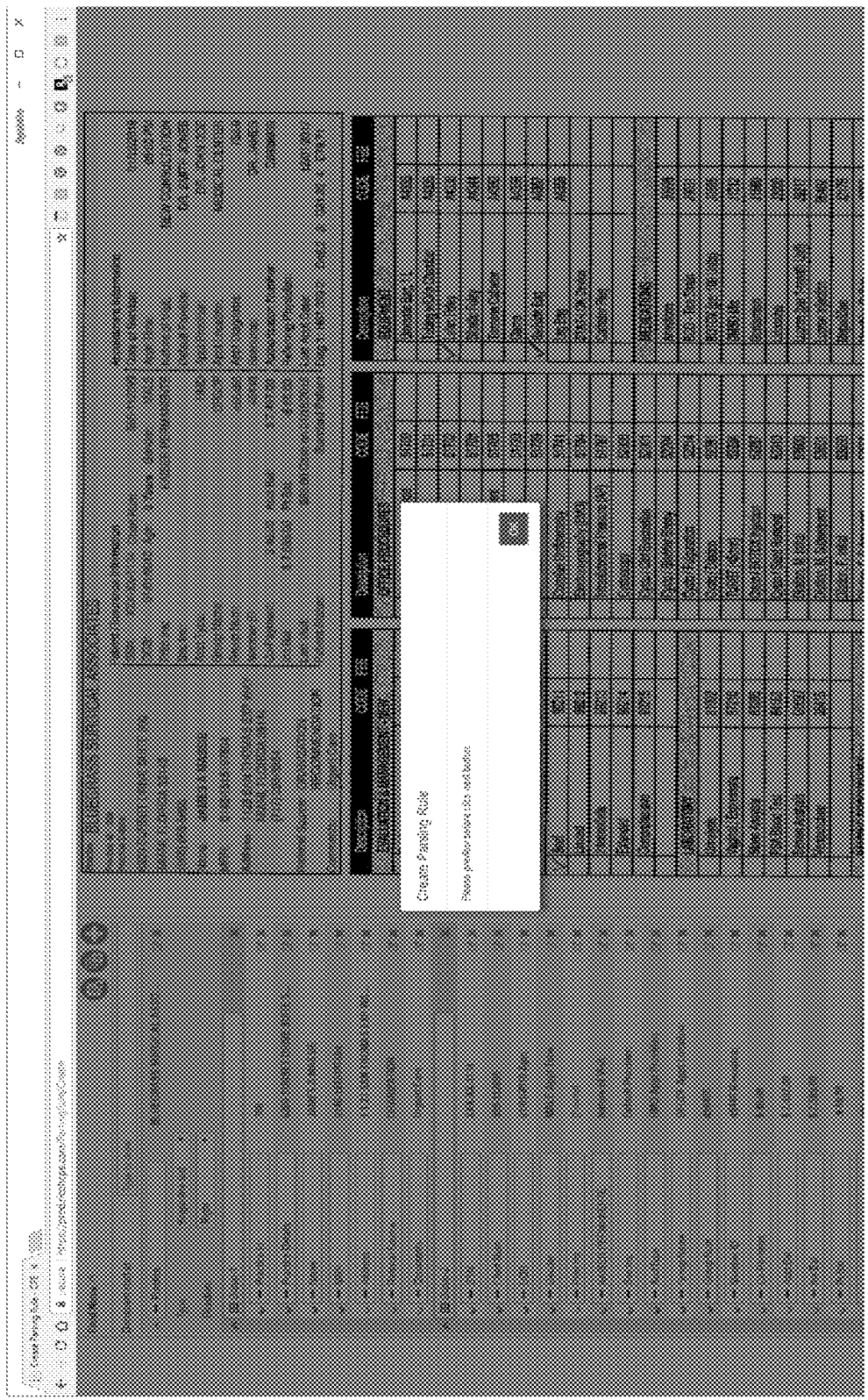
FIG. 4K is a user interface screen that allows a user to preview the created parsing rule before submitting it.

In step 312, Cloud EMR Application Manager 160 sends Web content data including results of extracting. FIG. 4I is a user interface screen 420 that displays the data in the data fields of the Superbill image that corresponds to the extracted one or more field labels selected by the user. In detail, in this example, the extracted one or more field labels 421A selected by the user and data in the data fields 421B of the Superbill image are displayed on the user interface screen 420 side-by-side. For example, in user interface screen 420, "Practice Id" is one of the one or more field labels, "308" is actual data in the data filed corresponding to "Practice Id." In step 314, Cloud EMR Application Manager 160 creates a parsing rule including the region information from which OCR will extract field label information. A parsing rule may further include bibliographic information, for example, Parsing rule name and Parsing rule description. This is the third step 405C of FIG. 4C, in which the user can provide such bibliographic information for the parsing rule. Cloud EMR Application Manager 160 stores the created parsing rule on CPE data 180 as Parsing rule data 182. FIG. 4J is a user interface screen 422 that allows a user to enter bibliographic information for the parsing rule. Parsing rule name and Description may be input into the user interface screen 422. FIG. 4K is a user interface screen 424 that allows a user to preview the created parsing rule before submitting it. This is the fourth and last step 405D of FIG. 4C, in which the user can preview the parsing rule before submitting it to be saved. In this example, field labels and corresponding data fields of the parsing rule are shown side-by-side with the Superbill image for the user to preview.

Some advantages of these parsing rule procedures are that they automate processing of EMR records and reduce the amount of data entry and time needed by a user in processing EMR records or that a user is able to create a parsing rule seeing a preview image of Superbill. Further, by using a storage service to upload actual captured Superbill image to a cloud system, a user is able to upload it easily by a user device, for example a personal computer, a smart device and etc. In addition, the supervised approach for creating parsing rules for processing Superbills increase accuracy, which in turn reduces the amount of computational resources required to process Superbills.

According to one embodiment, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques, or may include digital electronic devices such as at least one application-specific integrated circuit (ASIC) or field programmable gate array (FPGA) that is persistently programmed to perform the techniques, or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 5:
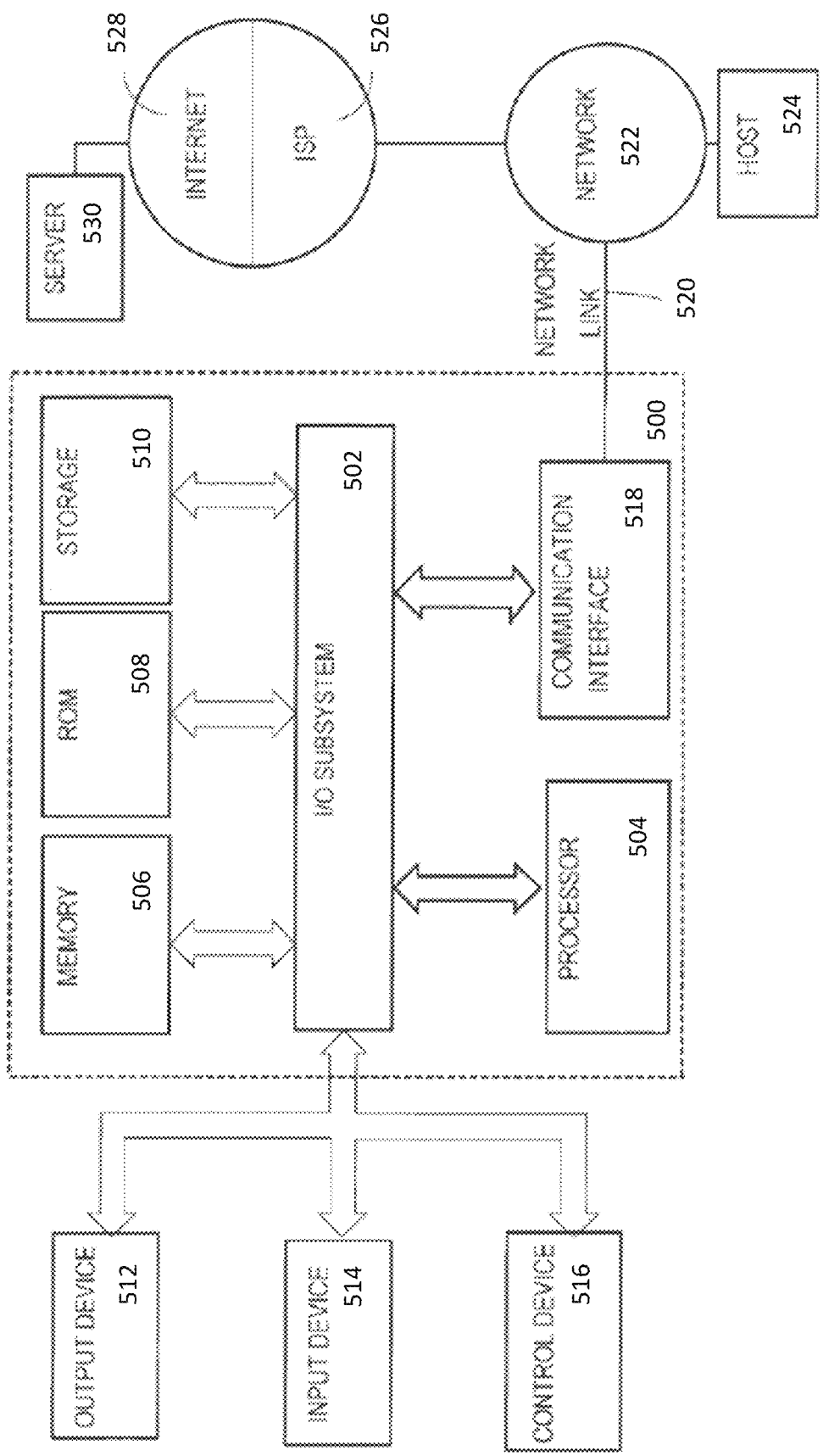
FIG. 5 is a block diagram that illustrates an example computer system with which an embodiment may be implemented.

FIG. 5 is a block diagram that illustrates an example computer system with which an embodiment may be implemented. In the example of FIG. 5, a computer system 500 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 500 includes an input/output (I/O) subsystem 502 which may include a bus and/or other communication mechanism(s) for communicating information and/or instructions between the components of the computer system 500 over electronic signal paths. The I/O subsystem 502 may include an I/O controller, a memory controller and at least one I/O port. The electronic signal paths are represented schematically in the drawings, for example as lines, unidirectional arrows, or bidirectional arrows.

At least one hardware processor 504 is coupled to I/O subsystem 502 for processing information and instructions. Hardware processor 504 may include, for example, a general-purpose microprocessor or microcontroller and/or a special-purpose microprocessor such as an embedded system or a graphics processing unit (GPU) or a digital signal processor or ARM processor. Processor 504 may comprise an integrated arithmetic logic unit (ALU) or may be coupled to a separate ALU.

Computer system 500 includes one or more units of memory 506, such as a main memory, which is coupled to I/O subsystem 502 for electronically digitally storing data and instructions to be executed by processor 504. Memory 506 may include volatile memory such as various forms of random-access memory (RAM) or other dynamic storage device. Memory 506 also may be used for storing temporary variables or other intermediate information during execution of instructions to be executed by processor 504. Such instructions, when stored in non-transitory computer-readable storage media accessible to processor 504, can render computer system 500 into a special-purpose machine that is customized to perform the operations specified in the instructions.

Computer system 500 further includes non-volatile memory such as read only memory (ROM) 508 or other static storage device coupled to I/O subsystem 502 for storing information and instructions for processor 504. The ROM 508 may include various forms of programmable ROM (PROM) such as erasable PROM (EPROM) or electrically erasable PROM (EEPROM). A unit of persistent storage 510 may include various forms of non-volatile RAM (NVRAM), such as FLASH memory, or solid-state storage, magnetic disk or optical disk such as CD-ROM or DVD-ROM, and may be coupled to I/O subsystem 502 for storing information and instructions. Storage 510 is an example of a non-transitory computer-readable medium that may be used to store instructions and data which when executed by the processor 504 cause performing computer-implemented methods to execute the techniques herein.

The instructions in memory 506, ROM 508 or storage 510 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JSON, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using structured query language (SQL) or no SQL, an object store, a graph database, a flat file system or other data storage.

Computer system 500 may be coupled via I/O subsystem 502 to at least one output device 512. In one embodiment, output device 512 is a digital computer display. Examples of a display that may be used in various embodiments include a touch screen display or a light-emitting diode (LED) display or a liquid crystal display (LCD) or an e-paper display. Computer system 500 may include other type(s) of output devices 512, alternatively or in addition to a display device. Examples of other output devices 512 include printers, ticket printers, plotters, projectors, sound cards or video cards, speakers, buzzers or piezoelectric devices or other audible devices, lamps or LED or LCD indicators, haptic devices, actuators or servos.

At least one input device 514 is coupled to I/O subsystem 502 for communicating signals, data, command selections or gestures to processor 504. Examples of input devices 514 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 516, which may perform cursor control or other automated control functions such as navigation in a graphical interface on a display screen, alternatively or in addition to input functions. Control device 516 may be a touchpad, a mouse, a trackball, or cursor direction keys for communicating direction information and command selections to processor 504 and for controlling cursor movement on display 512. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 514 may include a combination of multiple different input devices, such as a video camera and a depth sensor.

In another embodiment, computer system 500 may comprise an internet of things (IoT) device in which one or more of the output device 512, input device 514, and control device 516 are omitted. Or, in such an embodiment, the input device 514 may comprise one or more cameras, motion detectors, thermometers, microphones, seismic detectors, other sensors or detectors, measurement devices or encoders and the output device 512 may comprise a special-purpose display such as a single-line LED or LCD display, one or more indicators, a display panel, a meter, a valve, a solenoid, an actuator or a servo.

When computer system 500 is a mobile computing device, input device 514 may comprise a global positioning system (GPS) receiver coupled to a GPS module that is capable of triangulating to a plurality of GPS satellites, determining and generating geo-location or position data such as latitude-longitude values for a geophysical location of the computer system 500. Output device 512 may include hardware, software, firmware and interfaces for generating position reporting packets, notifications, pulse or heartbeat signals, or other recurring data transmissions that specify a position of the computer system 500, alone or in combination with other application-specific data, directed toward host 524 or server 530.

Computer system 500 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 500 in response to processor 504 executing at least one sequence of at least one instruction contained in main memory 506. Such instructions may be read into main memory 506 from another storage medium, such as storage 510. Execution of the sequences of instructions contained in main memory 506 causes processor 504 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 510. Volatile media includes dynamic memory, such as memory 506. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 502. Transmission media can also take the form of acoustic or light waves, such as those generated during radio-wave and infra-red data communications.

Various forms of media may be involved in carrying at least one sequence of at least one instruction to processor 504 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 500 can receive the data on the communication link and convert the data to a format that can be read by computer system 500. For instance, a receiver such as a radio frequency antenna or an infrared detector can receive the data carried in a wireless or optical signal and appropriate circuitry can provide the data to I/O subsystem 502 such as place the data on a bus. I/O subsystem 502 carries the data to memory 506, from which processor 504 retrieves and executes the instructions. The instructions received by memory 506 may optionally be stored on storage 510 either before or after execution by processor 504.

Computer system 500 also includes a communication interface 518 coupled to bus 502. Communication interface 518 provides a two-way data communication coupling to network link(s) 520 that are directly or indirectly connected to at least one communication networks, such as a network 522 or a public or private cloud on the Internet. For example, communication interface 518 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 522 broadly represents a local area network (LAN), wide-area network (WAN), campus network, internetwork or any combination thereof. Communication interface 518 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 518 sends and receives electrical, electromagnetic or optical signals over signal paths that carry digital data streams representing various types of information.

Network link 520 typically provides electrical, electromagnetic, or optical data communication directly or through at least one network to other data devices, using, for example, satellite, cellular, Wi-Fi, or BLUETOOTH technology. For example, network link 520 may provide a connection through a network 522 to a host computer 524.

Furthermore, network link 520 may provide a connection through network 522 or to other computing devices via internetworking devices and/or computers that are operated by an Internet Service Provider (ISP) 526. ISP 526 provides data communication services through a world-wide packet data communication network represented as internet 528. A server computer 530 may be coupled to internet 528. Server 530 broadly represents any computer, data center, virtual machine or virtual computing instance with or without a hypervisor, or computer executing a containerized program system such as DOCKER or KUBERNETES. Server 530 may represent an electronic digital service that is implemented using more than one computer or instance and that is accessed and used by transmitting web services requests, uniform resource locator (URL) strings with parameters in HTTP payloads, API calls, app services calls, or other service calls. Computer system 500 and server 530 may form elements of a distributed computing system that includes other computers, a processing cluster, server farm or other organization of computers that cooperate to perform tasks or execute applications or services. Server 530 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server 530 may comprise a web application server that hosts a presentation layer, application layer and data storage layer such as a relational database system using structured query language (SQL) or no SQL, an object store, a graph database, a flat file system or other data storage.

Computer system 500 can send messages and receive data and instructions, including program code, through the network(s), network link 520 and communication interface 518. In the Internet example, a server 530 might transmit a requested code for an application program through Internet 528, ISP 526, local network 522 and communication interface 518. The received code may be executed by processor 504 as it is received, and/or stored in storage 510, or other non-volatile storage for later execution.

The execution of instructions as described in this section may implement a process in the form of an instance of a computer program that is being executed, and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 504. While each processor 504 or core of the processor executes a single task at a time, computer system 500 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

What is claimed is:

1. An apparatus, comprising:
one or more processors, and
one or more memories communicatively coupled to the one or more processors, the one or more memories storing instructions which, when processed by the one or more processors, cause:
receiving source data of a sample Superbill via one or more computer networks from a client device;
creating parsing rule data for parsing Superbills that is based on the received source data of the sample Superbill by a user operation on the client device, the parsing rule data including at least region information where data in one or more data fields of the Superbill should be extracted and one or more field labels to be associated with the extracted data in the one or more data fields, the one or more field labels being managed by a first external system which manages Superbill data;
accessing, via the one or more computer networks, to a second external system which is configured to store data, to detect whether captured Superbill image data has been stored, wherein the captured Superbill image data represents a plurality of Superbills;
in response to detecting that the captured Superbill image data has been stored, obtaining the captured Superbill image data via the one or more computer networks from the second external system;
parsing the captured Superbill image data that represents a plurality of Superbills using the created parsing rule data;
generating output data based on results of parsing the obtained image data; and
sending the output data to the first external system via the one or more computer networks.

2. The apparatus as recited in claim 1, wherein the instructions further cause:
sending a web content including a preview image of the source data of the sample Superbill via the one or more computer networks to the client device; and
wherein the user operation on the client device includes a region selecting operation on the preview image displayed on the client device for the region information.

3. The apparatus as recited in claim 1, wherein the parsing parses the captured Superbill image data by performing OCR to the captured Superbill image data based on the region information included in the parsing rule and extracting the data in the one or more data fields from a result of OCR.

4. The apparatus as recited in claim 3, wherein the output data includes an association between the one or more field labels managed by the first external system and the data in the one or more data fields extracted from the result of OCR.

5. The apparatus as recited in claim 1, wherein the accessing the second external system is performed at predetermined timing by polling.

6. The apparatus as recited in claim 1, wherein the sending sends the output data and the captured Superbill image data respectively via different interfaces.

7. The apparatus as recited in claim 6, wherein the different interfaces include a Web API and FTP, and the sending sends the output data via the Web API and the captured Superbill image data via the FTP.

8. A method comprising:
receiving source data of sample Superbill via one or more computer networks from a client device;
creating parsing rule data for parsing Superbills that is based on the received source data of the sample Superbill by a user operation on the client device, the parsing rule data including at least region information where data in one or more data fields of the Superbill should be extracted and one or more field labels to be associated with the extracted data in the one or more data fields, the one or more field labels being managed by a first external system which manages Superbill data;
accessing, via the one or more computer networks, to a second external system which is configured to store data, to detect whether captured Superbill image data has been stored, wherein the captured Superbill image data represents a plurality of Superbills;
in response to detecting that the captured Superbill image data has been stored, obtaining the captured Superbill image data via the one or more computer networks from the second external system;
parsing the captured Superbill image data that represents a plurality of Superbills using the created parsing rule data;
generating output data based on results of parsing the obtained image data; and
sending the output data to the first external system via the one or more computer networks.

9. The method as recited in claim 8, further comprising:
sending a web content including a preview image of the source data of the sample Superbill via the one or more computer networks to the client device; and
wherein the user operation on the client device includes a region selecting operation on the preview image displayed on the client device for the region information.

10. The method as recited in claim 8, wherein the parsing parses the captured Superbill image data by performing OCR to the captured Superbill image data based on the region information included in the parsing rule and extracting the data in the one or more data fields from a result of OCR.

11. The method as recited in claim 10, wherein the output data includes an association between the one or more field labels managed by the first external system and the data in the one or more data fields extracted from the result of OCR.

12. The method as recited in claim 8, wherein the accessing the second external system is performed at specified times by polling.

13. The method as recited in claim 8, wherein the sending sends the output data and the captured Superbill image data respectively via different interfaces.

14. The method as recited in claim 13, wherein the different interfaces include a Web API and FTP, and the sending sends the output data via the Web API and the captured Superbill image data via the FTP.

15. One or more non-transitory computer-readable media providing an improvement in a first external system which manages Superbill data, the one or more non-transitory computer-readable media storing instructions which, when proceeded by one or more processors, cause:

a Web application executing on an apparatus to perform:
receiving source data of sample Superbill via one or more computer networks from a client device;
creating parsing rule data for parsing Superbills that is based on the received source data of the sample Superbill by a user operation on the client device, the parsing rule data including at least region information where data in one or more data fields of the Superbill should be extracted and one or more field labels to be associated with the extracted data in the one or more data fields, the one or more field labels being managed by a first external system which manages Superbill data;
accessing, via the one or more computer networks, to a second external system which is configured to store data, to detect whether captured Superbill image data has been stored, wherein the captured Superbill image data represents a plurality of Superbills;
in response to detecting that the captured Superbill image data has been stored, obtaining the captured Superbill image data via the one or more computer networks from the second external system;
parsing the captured Superbill image data that represents a plurality of Superbills using the created parsing rule data;
generating output data based on results of parsing the obtained image data; and
sending the output data to the first external system via the one or more computer networks.

16. The one or more non-transitory computer-readable media as recited in claim 15, further cause the Web application to perform:
sending a web content including a preview image of the source data of the sample Superbill via the one or more computer networks to the client device; and
wherein the user operation on the client device includes a region selecting operation on the preview image displayed on the client device for the region information.

17. The one or more non-transitory computer-readable media as recited in claim 15, wherein the parsing parses the captured Superbill image data by performing OCR to the obtained image data based on the region information included in the parsing rule and extracting the data in the one or more data fields from a result of OCR.

18. The one or more non-transitory computer-readable media as recited in claim 17, wherein the output data includes an association between the one or more field labels managed by the first external system and the data in the one or more data fields extracted from the result of OCR.

19. The one or more non-transitory computer-readable media as recited in claim 15, wherein the accessing the second external system is performed at specified times by polling.

20. The one or more non-transitory computer-readable media as recited in claim 15, wherein the sending sends the output data and the captured Superbill image data respectively via different interfaces.

* * * * *